United States Patent [19]

Murphy et al.

[11] Patent Number: 5,658,851
[45] Date of Patent: Aug. 19, 1997

[54] LIPOPHILIC SILOXANES AS ADJUVANTS FOR AGRICULTURE

[75] Inventors: Gerald J. Murphy, Hopewell Junction; George A. Policello, Peekskill, both of N.Y.

[73] Assignee: OSi Specialties, Inc., Danbury, Conn.

[21] Appl. No.: 422,385

[22] Filed: Apr. 14, 1995

Related U.S. Application Data

[63] Continuation-in-part of Ser. No. 135,916, Oct. 13, 1993, Pat. No. 5,561,099.

[51] Int. Cl.$^6$ ............... A01N 25/02; A01N 55/10
[52] U.S. Cl. ............ 504/116; 504/118; 71/DIG. 1; 424/405; 514/63
[58] Field of Search ................ 514/63; 504/116, 504/118; 71/DIG. 1

[56] References Cited

U.S. PATENT DOCUMENTS

| | | | |
|---|---|---|---|
| 3,299,112 | 1/1967 | Bailey | 260/448.2 |
| 4,155,995 | 5/1979 | Heinz et al. | 514/63 |
| 4,171,267 | 10/1979 | McAfee et al. | 428/391 |
| 4,337,166 | 6/1982 | Hill et al. | 510/122 |
| 4,514,319 | 4/1985 | Kulkarni et al. | 252/321 |
| 4,654,328 | 3/1987 | Itoh et al. | 514/63 |
| 5,045,225 | 9/1991 | Aronson et al. | 510/466 |
| 5,104,647 | 4/1992 | Policello | 514/772 |
| 5,145,879 | 9/1992 | Budnik et al. | 521/112 |

FOREIGN PATENT DOCUMENTS

| | | |
|---|---|---|
| 0121210 | 10/1984 | European Pat. Off. . |
| 2333442 | 1/1977 | France . |

OTHER PUBLICATIONS

Food Chem. 1986, pp. 34, 235–238.
Silicon., Chem. & Tech., CRC Press 1991, pp. 1–6 & 114–118.
Chemical Abstract; vol. 116, 1992, p. 436.
Organosilicone Surfactants As Adjuvants For Agrochemicals; Peter JG Stevens; pp. 103–122; Pesticide Science, 1993, (38).

*Primary Examiner*—José G. Dees
*Assistant Examiner*—Brian G. Bembenick
*Attorney, Agent, or Firm*—Scully, Scott, Murphy & Presser

[57] ABSTRACT

The present invention teaches the use of novel lipophilically modified organosilicone materials and their use as agricultural adjuvants with carrier oils. The lipophilically modified silicones (LMS) of the present invention include linear organosilicone compounds or certain cyclic organosilicone compounds of the formulae: $R_a(Me)_{3-a}Si\text{-}[OSi(Me)_2]_x\text{-}[OSi(Me)R]_y\text{-}OSi(Me)_{3-a}R_a$ wherein a=0 or 1; when a=0, x=0 to 4, y=1 to 4, and when a=1, x=0 to 4, and y=0 to 4, provided that the sum of x+y is $\leq 6$; or (b)

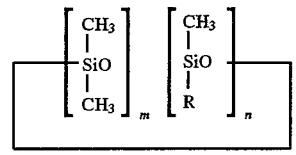

where m is 0 to 4, and n is 1 to 5, provided that m+n=3 to 5. R is the lipophilic group and may be an aryl, substituted aryl, aralkyl, alkyl phenyl ether, substituted alkyl phenyl ether or an alkyl alkyleneoxide group. The compounds potentiate spreading of mineral or vegetable oils or oil-containing emulsions in dormant spray oils, crop oil concentrates, pesticides, and the like on difficult-to-wet surfaces such as waxy leaf cuticles and arthropod exoskeletons.

19 Claims, No Drawings

LIPOPHILIC SILOXANES AS ADJUVANTS FOR AGRICULTURE

This application is a continuation in part of U.S. patent application Ser. No. 08/135,916, filed Oct. 13, 1993, U.S. Pat. No. 5,561,099.

BACKGROUND OF THE INVENTION

Many useful oil-based agricultural chemicals are less effective than desired because they do not spread well. It is typical to apply oil-based chemicals using a carrier such as a mineral or vegetable oil, or to apply dormant oils as aqueous sprays. The bulk surface tension of a liquid plays a key role in its ability to spread on hydrophobic surfaces such as the waxy cuticle of a leaf or the exoskeleton of an arthropod. If the surface tension of a liquid is not sufficiently low, the droplet will not spread effectively. Thus, there is a need for adjuvants which reduce the surface tension of lipophilic liquids and, thereby, increase the effectiveness of oil-based agricultural chemicals.

The use of oils as adjuvants or carriers for agricultural applications is well known. Petroleum and vegetable oils have been used in formulations for dormant spray oils, in preparations for the management of insects and mites including those that suffocate arthropod pests by clogging their spiracles, in crop oil concentrates and crop oils, and in emulsifiable concentrates. One of the effects of the oil is to increase the penetration of pesticides into the target organism. In addition, the oils often enhance spreading on target surfaces, which increases the effectiveness of the pesticide being applied.

According to P. J. McCall, et al. (*J. Agric. Food Chem.,* 34(2), 235–8), the addition of a crop oil concentrate (COC) to atrazine spray solutions significantly increased the amount of pesticide absorbed by giant foxtail sprayed with the chemical. Typically, 30% of the applied chemical penetrated the leaf in the presence of COC, while only 10% penetrated without COC. Kulkarni, et al. (U.S. Pat No. 4,514,319) disclosed relatively high molecular weight lipophilically modified silicones that, when used in connection with organosilicone surfactants, reduced the surface tension of hydrocarbon oils containing hydrophobic fillers, thus providing high efficiency antifoam compositions. U.S. Pat. No. 5,045,225 to Aronson, et al., disclosed the use of alkylaminosilicones that were soluble in mineral oil and resulted in enhanced surface activity. The compounds imparted self-hydrophobizing properties to antifoam compositions containing hydrophilic mineral particles such as silica.

U.S. Pat. No. 4,171,267 to McAfee, et al. disclosed an organopolysiloxane fluid as a component of a miscible composition for lubricating organic fibers that contained a hydrocarbon oil and a bridging agent obtained by reacting an organopolysiloxane with a long chain alcohol.

SUMMARY OF THE INVENTION

Taught herein are novel oil-based agricultural adjuvant compositions which are a mixture of about 1% to about 99% by weight of a linear or cyclic lipophilically modified silicone, or a mixture thereof, and from about 99% to about 1% by weight of an oil carrier, such as paraffinic or aromatic-based mineral oils, animal or vegetable oils or water insoluble pesticides which may act as carriers. These oil-based compositions containing a lipophilically modified silicone exhibit improved spreading properties. The compositions of the present invention may also include a pesticide such as herbicides, fungicides and insecticides, or mixtures thereof.

DETAILED DESCRIPTION OF THE INVENTION

The present invention provides a lipophilically modified silicone/carrier oil composition that gives improved spreading properties relative to the carrier oil alone. This invention also provides a lipophilically modified silicone/carrier oil composition that exhibits lower non-aqueous surface tension values than the carrier oil alone. The present invention provides a homogeneous composition that gives increased foam control relative to formulations based on the carrier oil alone. This invention also yields a crop oil concentrate composition containing a lipophilically modified silicone spreading agent.

The lipophilically modified silicones (LMS) of the present invention, which are present at 1 to 99, preferably 1 to 25, and most preferably 1 to 10, weight percent of the composition, include linear organosilicone compounds (LOS) or certain cyclic organosilicone compounds (COS). The LOS of the present invention have the general formula:

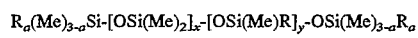

wherein a=0 or 1; and when a=0, x=0 to 4, preferably 0 to 1, most preferably 0, and y=1 to 4, preferably 1 to 2, most preferably 1; and when a=1, x=0 to 4, preferably 0 to 2, most preferably 1 to 2, and y=0 to 4, preferably 0 to 2, most preferably 0, provided that the sum of x+y is ≦6. R is the lipophilic group and may be an aryl, substituted aryl, aralkyl, alkyl phenyl ether, substituted alkyl phenyl ether or an alkyl alkyleneoxide group, and each R may be the same or different.

When R is an aryl, substituted aryl, aralkyl, alkylphenyl ether or substituted alkyl phenyl ether it conforms to the general formula $C_bH_{2b}O_pC_6H_cX_{5-c}$, wherein b=0 to 8, preferably 2 to 4, p=0 or 1, c=2 to 5, and X is a hydroxy or alkyl or alkoxy group having 1 to 12 carbon atoms which may have substituents thereon, provided that when b=0, p=0. When R is alkyl alkyleneoxide it conforms to the general formula $C_bH_{2b}O(C_dH_{2d}O)_eR^1$ wherein b=2 to 8, preferably 2 to 4, d=3 to 4, preferably 3, and e=1 to 5, preferably 2 to 3, and $R^1$ is hydrogen, an alkyl radical with 1 to 4 carbons, aryl, aralkyl or acetyl. R and $R^1$ may be the same or different on any given molecule. Preferred R groups are alkyl phenyl ethers, aralkyl with phenylethyl group and 2-methoxy- 4-(2-propyl) phenol (a eugenol derivative). The important issue is that R promote the solubility of the LOS in the oil matrix.

COS of the present invention are of the structure:

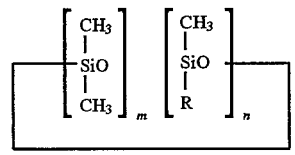

where m is 0 to 4, preferably 0 to 2, and n is 1 to 5, preferably 3 to 5, most preferably 4 to 5, provided that m+n=3 to 5, and R is defined above.

When R is hydrocarbon, the content of the hydrocarbon component is ≦55% by weight of the lipophilic silicone compound. When R is an alkyl alkyleneoxide group, the alkyl alkyleneoxide content is ≦60% by weight of the lipophilic silicone compound. For LOS, the weight percent (denoted below as wt %) lipophile is defined as:

$$\text{wt \% Lipophile} = \frac{(MW\,\text{Lipophile})y}{162.38 + 74.15x + y(60.13 + MW\,\text{Lipophile})} \times 100$$

and for COS the weight percent lipophile is defined as:

$$\text{wt \% Lipophile} = \frac{(MW\,\text{Lipophile})n}{74.15m + n(60.13 + MW\,\text{Lipophile})} \times 100$$

wherein MW is the molecular weight of the lipophilic group (R).

For linear structures, the degree of polymerization (DP) is defined as the total value of x+y+2, which represents the number of siloxane units in the silicone copolymer including its two end groups. Preferred LOS have a DP of $\leq 8$, preferably 3 to 5. For cyclic structures DP=m+n, and the COS of the present invention preferably have a DP of 3 to 5.

The carrier oil of the invention, which is present at 99 to 1 weight percent, is comprised of oils and mixtures thereof, selected from paraffinic, isoparaffinic and cycloparaffinic mineral oils, vegetable oils, such as soybean oil, canola oil, castor oil, palm oil, olive oil, corn oil, cottonseed oil, sesame seed oil and the like. In addition, methylated oils, such as methylated soybean oil, methyl palmitate, methyl oleate, and the like are also suitable carrier oils. Mixtures of mineral, vegetable and/or methylated oils may also be employed. The carrier oil may itself be an active ingredient, e.g., a pesticide.

Exemplary mineral oils are those marketed under the trade names EXXOL®, ISOPAR®, NORPAR® and ORCHEX® from Exxon Chemical (Houston, Tex.). Methylated oils such as the methylated soybean oil are available from Henkel, Canada, under the product name "Emery 2235, Distilled Methylsoyate." One skilled in the art would be able to determine other suitable oils from this listing.

An exemplary composition of the present invention comprises from about 1% to about 99% by weight of LMS, has a DP of $\leq 8$, and a hydrocarbon content of $\leq 55\%$, or an alkylalkyleneoxide content of $\leq 60\%$ and a carrier oil present from about 99% to about 1% by weight of the composition.

Optionally, the composition can include from about 0.1% to about 2.5% by weight of a hydrophobized silica filler, for example, TULLANOX® 500 (Tulco), and AEROSIL® R-812 (Degussa). The composition may also include a nonionic surfactant that is present from about 1 to about 50% by weight. Examples of suitable nonionic surfactants are those that are soluble in the lipophilically modified silicone/carrier oil matrix, and having an HLB between 8 and 17, for example, branched tridecyl alcohol ethoxylate. When the composition contains the optional ingredients, the silicone/carrier oil mixture makes up the balance of the composition, with the ratio of the silicone/carrier oil portion 99:1 to 1:99. Other optional ingredients are pesticides, as discussed below.

The composition is prepared by combining the components in the desired ratio, consistent with the guidelines described above, and mixing these ingredients according to conventional methods that will provide a clear to slightly hazy, uniform product. Mixing by a mechanical agitator or a mechanical shaker are examples of such methods. When the optional filler is included in the composition the ingredients are combined using a high shear mixer, such as a Lightnin' mixer.

The lipophilically modified silicone is useful as a spreading agent for oil-based adjuvants such as crop oil concentrates, dormant oils, and non-aqueous, ultra-low volume oil sprays, where the pesticide is dispersed or dissolved in the carrier oil. In addition, the lipophilically modified silicones of the present invention are useful as spreading agents when incorporated into oil-based pesticide formulations, such as emulsifiable concentrates. The lipophilically modified silicone compounds of this invention promote the spreading of the carrier oil or oil soluble pesticides on plant and/or arthropod surfaces.

By "pesticide" is meant any compound used to destroy pests, including herbicides, fungicides, insecticides, rodenticides and the like. The term specifically includes oily materials not otherwise toxic, material used as pesticides in the destruction of aphids, scale insects, weeds, and the like. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed.

More specific examples of pesticide compounds that can be used in the compositions of the invention are: phenoxy acetic acids, phenoxy propionic acids, phenoxy butyric acids, benzoic acids, triazines and s-triazines, substituted ureas, uraciis, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofopmethyl, fenoxaprop-ethyl, fluazifop-p-butyl, haloxyfop-methyl, quizalofop, sethoxydim, dichlobenil, isoxaben, and bipyridylium compounds.

EXAMPLES

The following examples are presented to further illustrate and explain the present invention and should not be taken as limiting in any regard. Unless otherwise indicated, all parts and percentages are by weight, and are based on the weight at the particular stage of the processing being described.

Example 1

The preparation of LMS is described in this example. The SiH intermediates were prepared by acid equilibration as outlined in *Silicones, Chemistry and Technology* (CRC Press, 1991, pages 1 to 6), and U.S. Pat. No. 5,145,879 to Budnik, et al., which are incorporated herein by reference.

The intermediates then were used to prepare a number of LMS. A 500 mL reaction vessel containing 134.1 g (0.603 moles) of an SiH intermediate ($Me_3SiO[MeSi(H)O]SiMe_3$) was heated to 60° C., while under a nitrogen blanket. Next 0.04 cc of platinum catalyst solution (0.16 g catalyst in 10 g toluene) along with 9.1 g (0.087 moles) styrene. (The catalyst compound contains 3.5% Pt as a divinyltetramethyldisiloxane platinum complex dissolved in a vinyl end-blocked siloxane). The initial reaction gave a 9° C. exotherm. The remainder of the catalyst (0.28 cc, corresponding to a total catalyst charge of 5.6 ppm Pt) and the styrene (55.3 g; 0.531 moles) were added at a rate that kept the temperature controlled below 85° C. After the addition, the mixture was allowed to stir for one hour at 70° C. The reaction mixture showed no traces of SiH when introduced to a fermentation tube containing KOH/water/ethanol solution. The product was then filtered through a fine filter pad and stripped on a Rotovap for 1.5 hours at 70° C. to 1.0 mm Hg to afford a clear light amber liquid with a Brookfield (spindle LV-2, 60 rpm) viscosity of 10 cps at 25° C., shown as LMS-1 in Table 1.

Using this procedure, various lipophilically modified silicones (LMS) of the general structure $R_a(Me)_{3-a}Si\text{-}[OSi(Me)_2]_x\text{-}[OSi(Me)R]_y\text{-}OSi(Me)_{3-a}R_a$ wherein the values for a, x, y, and R, the type of lipophile contained in the LMS, are varied as listed in Table 1 below.

TABLE 1

Structures of Lipophilically Modified Silicones

| Compound | a | x | y | Lipophilic Group (R) | % Lipophile |
|---|---|---|---|---|---|
| LMS-1 | 0 | 0 | 1 | $C_2H_4(C_6H_5)$ | 32.1 |
| LMS-2 | 0 | 0 | 1 | $C_3H_6O(C_6H_5)$ | 37.8 |
| LMS-3 | 0 | 0 | 1 | $C_3H_6(C_3H_6O)_2H$ | 43.9 |
| LMS-4 | 0 | 0 | 1 | $C_3H_6(C_3H_6O)_3H$ | 51.0 |

As comparative examples, organomodified silicone copolymers having the formula $(Me)_3Si-[OSi(Me)_2]_x-[OSi(Me)R^1]_y-[OSi(Me)R^2]_z-OSi(Me)_3$ were prepared as described in U.S. Pat. Nos. 2,834,748 and 3,507,815, and the CRC Silicones book cited above at pages 114 to 115, with values for the structural variables of the compounds as outlined in Table 2 below.

TABLE 2

Variables for Comparative Structures

| Compound | x | y | z | Pendant R Group | % Lipophile |
|---|---|---|---|---|---|
| SIL-A | 80 | 8 | 0 | $R^1 = C_{10}H_{21}$ | 12.0 |
| SIL-B | 50 | 30 | 0 | $R^1 = C_{10}H_{21}$ | 42.6 |
| SIL-C | 120 | 40 | 0 | $R^1 = C_{12}H_{25}$ | 37.0 |
| SIL-D | 0 | 0 | 1 | $R^2 = C_3H_6O(CH_2CH(CH_3)O)_{13}C_4H_9$ | 79.6 |
| SIL-E | 5 | 5 | 5 | $R^1 = C_{12}H_{25}$ $R^2 = C_3H_6O(CH_2CH_2O)_8CH_3$ | 20.5 |

Example 2

This example demonstrates the solubility of the LMS prepared in Example 1 in mineral oil and in a variety of vegetable oils, compared to the organomodified silicones (denoted SIL-A through SIL-E) prepared in Example 1. The solubilities of the LMS samples and the comparative samples were examined by making a 1:1 mixture of the silicone with each of the following carrier oils: mineral oil (denoted A in the Table below, a white mineral oil obtained from Gloria, Witco Corp., New York, N.Y. having a viscosity of 39–42 cSt at 40° C.; Sp. gr.=0.859–0.880 at 25° C.), methylated soybean oil (denoted B below, obtained from Henkel Canada, Ltd, Mississauba, Ontario), and soybean oil (denoted C). All the LMS compounds were either completely soluble or readily formed stable dispersions in each of the three oils.

TABLE 3

Solubility[a] of Lipophilically Modified Silicones in Carrier Oils

| Compound | Oil A | Oil B | Oil C |
|---|---|---|---|
| LMS-1 | D | S | S |
| LMS-2 | S | S | S |
| LMS-3 | S | S | S |
| LMS-4 | D | S | S |
| SIL-A | I | I | I |
| SIL-B | S | S | I |
| SIL-C | S | S | I |
| SIL-D | I | S | S |
| SIL-E | I | S | S |

[a] I = insoluble; D = dispersible; and S = soluble.

Similar solubility results are expected for canola oil, castor oil, palm oil, safflower oil, and methylated vegetable oils. For example, LMS-1 in a 1:1 mixture is soluble in both canola oil and safflower oil.

Example 3

This example demonstrates that the LMS reduces the surface tension of carrier oils, such as soybean oil, to a greater extent than oil-soluble polyalkyleneoxide-modified silicones with greater than 5 propylene oxide units (PO) (denoted SIL-D in the table below). The surface tension of silicone/oil blends was measured by the Wilhelmy plate method at 25° C., using a sandblasted platinum blade as the sensor, to obtain values set out in Table 4 below.

TABLE 4

Surface Tension of LMS versus Comparative Silicones in Soybean Oil at Various Concentrations

| WT. % LMS | LMS-1 | LMS-3 | LMS-4 | SIL-D |
|---|---|---|---|---|
| 0 | 33.9 | 33.9 | 33.9 | 33.9 |
| 1 | — | — | 33.4 | 34.2 |
| 5 | — | — | 31.5 | 33.9 |
| 10 | — | — | 30.1 | 33.2 |
| 25 | 23.7 | 25.5 | — | 32.9 |
| 50 | — | — | 25.6 | 31.0 |
| 100 | 22.3 | 22.6 | 24.2 | 31.4 |

Example 4

The spreading performance of compositions of the invention was evaluated in and was determined by applying a 10 μL drop of the silicone oil on a morningglory leaf (*Ipomoea hederacea*) using a micropipette, and measuring the spread diameter after 1 minute with a ruler. The following spread rating is used to describe the degree of spreading: 1=≧2 mm but ≦5 mm; 2=>5 mm but ≦10 mm; 3=>10 mm but ≦20 mm; 4=>20 mm but ≦30 mm; 5=>30 mm. Data are compared to control oil A, mineral oil (Gloria); oil B, methylated Soybean Oil (Emery); and oil C, soybean oil, as tabulated in Table 5 below.

The type of lipophilic group plays a role in spreading. This is demonstrated by comparing LMS-1 (phenethyl), and LMS-4 (3 PO) with Sil-D. LMS-1 and LMS-4 both provide good spreading properties there are clear differences in the spreading ability.

TABLE 5

Spreading of Lipophilically Modified Silicones on Morningglory.

| Compound | Spread Factor |
|---|---|
| LMS-1 | 5 |
| LMS-4 | 2 |
| SIL-D | 1 |
| OIL A | 1 |
| OIL B | 1 |
| OIL C | 1 |

Example 5

The ability of the LMS compounds to promote spreading of the oil carrier on a leaf surface is demonstrated in this example. LMS/oil blends are prepared in a 1:1 ratio by weighing equal amounts of material into a 2 dram vial. The components are shaken to provide a homogeneous mixture. The oil carriers consisted of mineral oil or methylated soybean oil. Spreading is evaluated on LMS/oil combinations, where the LMS is soluble in the oil carrier.

A 2 μL drop of the LMS/Oil mixture is applied to freshly excised leaf and allowed to spread for 30 seconds. A Poinsettia leaf was used as the test surface. The spread diameter of the droplet is measured using a mm ruler. Results are tabulated in Table 6 below.

TABLE 6

Spreading Ability of LMS/Oil Blends on Poinsettia Leaf
Spread Diameter (mm)

| Compound | Mineral Oil[a] |
|---|---|
| LMS-1 | 12.2 |
| LMS-2 | 14.0 |
| LMS-3 | 13.5 |
| LMS-4 | 12.5 |
| NONE | 5.8 |

[a]ORCHEX mineral oil

The data show that in all cases the addition of an LMS component of the present invention to the oil carrier increases the spread diameter of the oil droplet relative to the carrier oil alone.

Example 6

This example demonstrates that aqueous dispersions of agricultural oil compositions containing an LMS component, and a nonionic surfactant, spread to a greater extent than the comparative composition without the LMS component. Table 7 gives the compositions for the oil formulations used in this example. The surfactant provides self-dispersibility.

Dispersion of the formulations in Table 7 (1 wt %) were prepared in distilled water. A 100 μL droplet of the dispersion was applied to polyester film and allowed to air dry over 4 hours, at which time the spread diameter of the contained oil was measured.

TABLE 7

| Self Dispersing Oil Formulations | | | |
|---|---|---|---|
| Component | O-1 | O-2 | O-3 |
| LMS-1 | 10 | — | — |
| LMS-3 | — | 10 | — |
| ORCHEX 692 | 85 | 85 | 95 |
| TERGITOL NP-6 | 5 | 5 | 5 |
| Total | 100 | 100 | 100 |
| Spread Diameter (mm) | 44 | 51 | 33 |
| Relative Spread Area[(a)] | 158 | 212 | 89 | a. Area Relative to 100 μL droplet of Water

We claim:

1. An agricultural composition comprising from about 1% to about 99% by weight of an oil and from about 99% to about 1% by weight of an organosilicone compound of the formula $$R_a(Me)_{3-a}Si\text{-}(OSi(Me)_2)_x\text{-}(OSi(Me)R)_y\text{-}OSi(Me)_{3-a}R_a$$

wherein a=0 or 1; and when a=0, x=0 to 4 and y=1 to 4; and when a=1, x=0 to 4 and y=0 to 4;

provided that the sum of x+y is ≦6; and

R is a lipophilic group selected from the group consisting of: aryl, substituted aryl, aralkyl, alkyl phenyl ether, substituted alkyl phenyl ether and alkyl alkyleneoxide groups;

and each R may be the same or different.

2. A composition according to claim 1 wherein R is an aryl, substituted aryl, aralkyl, alkyl phenyl ether, or substituted alkyl phenyl ether of the general formula $C_bH_{2b}O_pC_6H_cX_{5-c}$, wherein b=0 to 8, p=0 or 1, c=2 to 5, and X is a hydroxy or alkyl or alkoxy group having 1 to 12 carbon atoms which may have substituents thereon, provided that when b=0, p=0.

3. A composition according to claim 1 wherein R is alkyl alkyleneoxide of the general formula $C_bH_{2b}O(C_dH_{2d}O)_eR^1$ wherein b=2 to 8, d=3 to 4, and e=1 to 5, and $R^1$ is hydrogen, an alkyl radical with 1 to 4 carbons, aryl, aralkyl or acetyl.

4. A composition according to claim 1 wherein R is selected from the group consisting of: alkyl phenyl ethers, aralkyl with a phenylethyl group and 2-methoxy-4-(2-propyl) phenol.

5. A composition according to claim 1 wherein the organosilicone is present at 1 to 25 percent by weight of the composition.

6. A composition according to claim 1 wherein the organosilicone has a degree of polymerization which is less than or equal to 8.

7. A composition according to claim 3 wherein R is present at ≦60% by weight of the organosilicone.

8. A composition according to claim 1 further comprising from about 1% to about 50% by weight of a nonionic surfactant that is soluble in the lipophilic silicone/oil composition and has an HLB between 8 and 17.

9. A composition according to claim 1 further comprising from about 0.1% to about 2.5% by weight of a hydrophobized silica filler.

10. A composition according to claim 1 wherein the composition additionally includes an oil soluble pesticide.

11. A composition according to claim 10 wherein the pesticide is selected from the group consisting of growth regulators, photosynthesis inhibitors, pigment inhibitors, mitotic disrupters, amino acid synthesis inhibitors, lipid biosynthesis inhibitors, cell wall inhibitors, and cell membrane disrupters.

12. A composition according to claim 11 wherein the oil is selected from the group consisting of mineral oils, vegetable oils, methylated oils, and mixtures thereof.

13. A composition according to claim 1 wherein a=0 and y=1.

14. A composition according to claim 3 wherein b=2 to 4, d=3 and e=2 to 3.

15. A method of treating a plant or arthropod with an oil-containing composition comprising applying to a plant or arthropod a composition comprising from about 1% to about 99% by weight of an oil and from about 1% to about 99% by weight of an organosilicone of the formula:

$$R_a(Me)_{3-a}Si\text{-}(OSi(Me)_2)_x\text{-}(OSi(Me)R)_y\text{-}OSi(Me)_{3-a}R_a$$

wherein a=0 or 1; and when a=0, x=0 to 4 and y=1 to 4; and when a=1, x=0 to 4 and y=0 to 4;

provided that the sum of x+y is ≦6; and

R is a lipophilic group selected from the group consisting of: aryl, substituted aryl, aralkyl, alkyl phenyl ether, substituted alkyl phenyl ether and alkyl alkyleneoxide groups; and each R may be the same or different.

16. A method according to claim 15 wherein the composition further comprises a pesticide.

17. A method according to claim 16 wherein the pesticide is selected from the group consisting of growth regulators, photosynthesis inhibitors, pigment inhibitors, mitotic disrupters, amino acid synthesis inhibitors, lipid biosynthesis inhibitors, cell wall inhibitors, and cell membrane disrupters.

18. A method according to claim 17 wherein the oil is selected from the group consisting of mineral oils, vegetable oils, methylated oils, and mixtures thereof.

19. A method according to claim 18 wherein the organosilicone has a degree of polymerization of ≦8.

* * * * *

REEXAMINATION CERTIFICATE (4719th)

United States Patent
Murphy et al.

(10) Number: US 5,658,851 C1
(45) Certificate Issued: Jan. 14, 2003

(54) LIPOPHILIC SILOXANES AS ADJUVANTS FOR AGRICULTURE

(75) Inventors: Gerald J. Murphy, Hopewell Junction, NY (US); George A. Policello, Peekskill, NY (US)

(73) Assignee: Witco Corporation, Greenwich, CT (US)

Reexamination Request:
No. 90/005,394, Jun. 17, 1999

Reexamination Certificate for:
Patent No.: 5,658,851
Issued: Aug. 19, 1997
Appl. No.: 08/422,385
Filed: Apr. 14, 1995

Related U.S. Application Data

(63) Continuation-in-part of application No. 08/135,916, filed on Oct. 13, 1993, now Pat. No. 5,561,099.

(51) Int. Cl.$^7$ .......................... A01N 25/02; A01N 55/10
(52) U.S. Cl. ...................... 504/362; 504/118; 424/405; 514/63; 514/789; 514/975
(58) Field of Search .................. 504/362, 118; 514/789, 975, 63; 424/405

(56) References Cited

U.S. PATENT DOCUMENTS

4,668,666 A    5/1987    Allan et al. .................... 514/63

*Primary Examiner*—S. Mark Clardy

(57) ABSTRACT

The present invention teaches the use of novel lipophilically modified organosilicone materials and their use as agricultural adjuvants with carrier oils. The lipophilically modified silicones (LMS) of the present invention include linear organosilicone compounds or certain cyclic organosilicone compounds of the formulae: $R_a(Me)_{3-a}Si-[OSi(Me)_2]_x-[OSi(Me)R]_y-OSi(Me)_{3-a}R_a$ wherein a=0 or 1; when a=0, x=0 to 4, y=1 to 4, and when a=1, x=0 to 4, and y=0 to 4, provided that the sum of x+y is $\leq 6$; or (b)

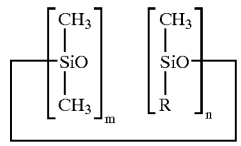

where m is 0 to 4, and n is 1 to 5, provided that m+n=3 to 5. R is the lipophilic group and may be an aryl, substituted aryl, aralkyl, alkyl phenyl ether, substituted alkyl phenyl ether or an alkyl alkyleneoxide group. The compounds potentiate spreading of mineral or vegetable oils or oil-containing emulsions in dormant spray oils, crop oil concentrates, pesticides, and the like on difficult-to-wet surfaces such as waxy leaf cuticles and arthropod exoskeletons.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 15 are determined to be patentable as amended.

Claims 3–14 and 16–19, dependent on an amended claim, are determined to be patentable.

New claims 20–26 are added and determined to be patentable.

1. An agricultural composition comprising from about 1% to about 99% by weight of an oil and from about 99% to about 1% by weight of an organosilicone compound of the formula

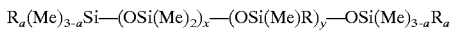

wherein a=0 or 1; and
  when a=0, x=0 to 4 and y=1 to 4; and
  when a=1, x=0 to 4 and y=0 to 4;
provided that the sum of x=y is $\leq 6$; and
R is a lipophilic group selected from the group consisting of: [aryl, substituted aryl, aralkyl,] alkyl phenyl ether, substituted alkyl phenyl ether and alkyl alkyleneoxide groups; and each R may be the same or different.

2. A composition according to claim 1 wherein R is an [aryl, substituted aryl, aralkyl,] alkyl phenyl ether, or substituted alkyl phenyl ether of the general formula $C_bH_{2b}O_pC_6H_cX_{5-c}$, wherein b=[0] *2* to [8] *4*, p=[0 or] *1*, c=2 to 5, and X is a hydroxy or alkyl or alkoxy group having 1 to 12 carbon atoms which may have substituents thereon[, provided that when b=0, p=0].

15. A method of treating a plant or arthropod with an oil-containing composition comprising applying to a plant or arthropod a composition comprising from about [1] *75%* to about 99% by weight of an oil and from about 1% to about [99] *25%* by weight of an organosilicone of the formula:

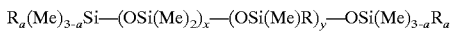

wherein a=0 or 1; and
  when a=0, x=0 to 4 and y=1 to 4; and
  when a=1, x=0 to 4 and y=0 to 4;
provided that the sum of x+y is $\leq 6$; and
R is a lipophilic group selected from the group consisting of: aryl, substituted aryl, aralkyl, alkyl phenyl ether, substituted alkyl phenyl ether and alkyl alkyleneoxide groups; and each R may be the same or different.

20. *An agricultural composition comprising from about 75% to about 99% by weight of an oil and from about 1% to about 25% by weight of an organosilicone of the formula:*

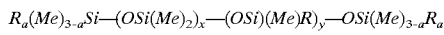

*wherein a=0 or 1; and*
  *when a=0, x=0 to 4 and y=1 to 4; and*
  *when a=1, x=0 to 4 and y=0 to 4;*
*provided that the sum of x=y is $\leq 6$; and*
*R is a lipophilic group selected from the group consisting of: aryl, substituted aryl, aralkyl, alkyl phenyl ether, substituted alkyl phenyl ether and alkyl alkyleneoxide groups; and each R may be the same or different.*

21. *A composition according to claim 20, wherein R is an aryl, substituted aryl, aralkyl, alkyl phenyl ether, or substituted alkyl phenyl ether of the general formula $C_bH_{2b}O_pC_6H_cX_{5-c}$, wherein b=0 to 8, p=0 or 1, c=2 to 5, and X is a hydroxy or alkyl or alkoxy group having 1 to 12 carbon atoms which may have substituents thereon, provided that when b=0, p=0.*

22. *A composition according to claim 20, wherein R is an alkyl alkyleneoxide of the general formula $C_bH_{2b}O(C_dH_{2d}O)_eR^1$ wherein b=2 to 8, d=3 to 4, and e=1 to 5, and $R^1$ is hydrogen, an alkyl radical with 1 to 4 carbons, aryl, aralkyl or acetyl.*

23. *A composition according to claim 20, wherein the composition further comprises an oil soluble pesticide.*

24. *A method according to claim 15, wherein R is an aryl, substituted aryl, aralkyl of the general formula $C_bH_{2b}O_pC_6H_cX_{5-c}$, wherein b=0 to 8, p=0 or 1, c=2 to 5, and X is a hydroxy or alkyl or alkoxy group having 1 to 12 carbon atoms which may have substituents thereon, provided that when b=0, p=0.*

25. *A method according to claim 15, wherein R is an alkyl phenyl ether or a substituted alkyl phenyl ether of the general formula $C_bH_{2b}O_pC_6H_cX_{5-c}$, wherein b=0 to 8, p=0 or 1, c=2 to 5, and X is a hydroxy or alkyl or alkoxy group having 1 to 12 carbon atoms which may have substituents thereon, provided that when b=0, p=0.*

26. *A method according to claim 15, wherein R is an alkyl alkyleneoxide of the general formula $C_bH_{2b}O(C_dH_{2d}O)_eR^1$ wherein b=2 to 8, d=3 to 4, and e=1 to 5, and $R^1$ is hydrogen, an alkyl radical with 1 to 4 carbons, aryl, aralkyl or acetyl.*

* * * * *